United States Patent [19]

Sticker

[11] 4,115,096
[45] Sep. 19, 1978

[54] DIHYDROPYRAZOLONE HERBICIDE
[75] Inventor: Robert Earl Sticker, Middleport, N.Y.
[73] Assignee: FMC Corporation, Philadelphia, Pa.
[21] Appl. No.: 848,632
[22] Filed: Nov. 4, 1977

Related U.S. Application Data

[63] Continuation of Ser. No. 685,741, May 13, 1976, abandoned.

[51] Int. Cl.$^2$ ..................... A01N 9/22; C07D 231/16
[52] U.S. Cl. ........................................ 71/92; 548/365
[58] Field of Search ............................ 71/92; 548/365
[56] References Cited

U.S. PATENT DOCUMENTS

| 454,223 | 6/1891 | Estermayer | 548/365 |
|---|---|---|---|
| 2,068,790 | 1/1937 | Brockmuhl et al. | 548/365 |
| 3,092,483 | 6/1963 | Perkow | 71/92 |

FOREIGN PATENT DOCUMENTS 19,576  8/1891  United Kingdom.

OTHER PUBLICATIONS

Vorbrodt, Chem. Abst., vol. 46, 8727s (1952).
Thompson et al., Botanical Gazette, vol. 107, p. 475 (1946).

*Primary Examiner*—Catherine L. Mills
*Attorney, Agent, or Firm*—Robert M. Kennedy; Robert L. Andersen; H. Robinson Ertelt

[57] ABSTRACT

The new herbicide, 2-cyclohexyl-4-iodo-1,5-dimethyl-1,2-dihydro-3H-pyrazol-3-one, is described and its preparation and use to control undesired plant growth are exemplified.

3 Claims, No Drawings

DIHYDROPYRAZOLONE HERBICIDE

This is a request for filing a continuation application under 37 CFR 1.60, of pending prior application Ser. No. 685,741, filed on May 13, 1976 abandoned.

BACKGROUND OF THE INVENTION

1. Field of the Invention

This invention pertains to the general field of herbicides and more specifically to a new compound useful in controlling undesired plant growth.

2. Description of the Prior Art

The 1,2-dihydro-3H-pyrazol-3-one subclass of dihydropyrazolones, of which the compound of the present invention is a member, has been known and studied extensively for a number of years. An important area of use of pyrazolones of this type has been in medicine, where 1,5-dimethyl-2-phenyl-1,2-dihydro-3H-pyrazol-3-one (antipyrine) and many of its analogs are employed for their analgetic, antirheumatic, antineuralgic and sedative properties. Herbicidal activity for one member of this subclass, 4-chloro-1,5-dimethyl-2-phenyl-1,2-dihydro-3H-pyrazole-3-one, and certain of its salts has been disclosed in U.S. Pat. No. 3,092,483. The 2-phenyl compound of the patent, being a 2-aryl-4-chloro-1,2-dihydro-3H-pyrazol-3-one, is chemically distinct from the compound of the present invention, a 2-cycloalkyl-4-iodo-1,2-dihydro-3H-pyrazol-3-one. U.S. Pat. No. 3,092,483, which claims herbicidal activity for the 4-chloro-2-phenyl compound, does not teach or suggest herbicidal activity for 2-cycloalkyl derivatives, much less the superior herbicidal activity of the 2-cyclohexyl-4-iodo derivative.

The outstanding plant responses in selective preemergence and postemergence herbicidal activity of the compound of the present invention have not previously been reported or suggested in the art.

SUMMARY OF THE INVENTION

This invention relates to a novel herbicidal compound, to new herbicidal compositions, and to a new method for the selective control of undesired plant growth. The compound of the present invention, 2-cyclohexyl-4-iodo-1,5-dimethyl-1,2-dihydro-3H-pyrazol-3-one, in pre- and postemergence applications, selectively controls undesired plant growth in the presence of certain crops, including corn, cotton, and peanuts. Effective control of the growth of a variety of grasses and broadleaved plant species is obtained with the compound of the present invention at rates below 1.12 kilograms per hectare. Herbicidal compositions containing the compound of the present invention may be utilized and applied by conventional methods.

DETAILED DESCRIPTION OF THE INVENTION

The new herbicide of this invention, 2-cyclohexyl-4-iodo-1,5-dimethyl-1,2-dihydro-3H-pyrazol-3-one, has the structural formula:

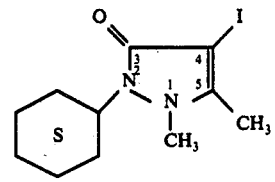

This compound, when formulated as the essential active ingr3edient in herbicidal compositions and utilized in either preemergence or postemergence application, has outstanding herbicidal properties. The compound of the present invention may be prepared from known materials by classical methods known to those skilled in the art. For example, the new herbicide may be prepared by the three-step sequence shown in the following scheme, wherein the new herbicide is designated III.

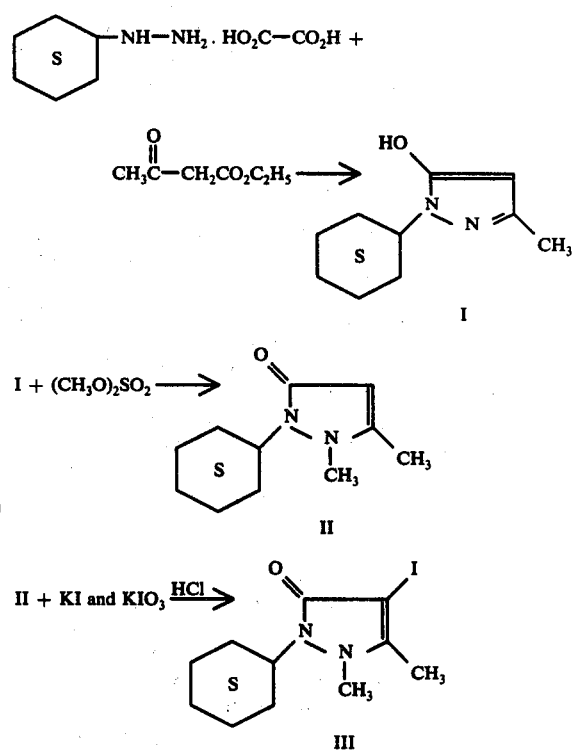

The intermediate 2-cyclohexyl-3-hydroxy-5-methyl-pyrazole, I, prepared by the reaction of cyclohexylhydrazine oxalate with ethyl acetoacetate, may be methylated with dimethyl sulfate to afford 2-cyclohexyl-1,5-dimethyl-1,2dihydro-3H-pyrazole-3-one, II, which upon iodination with potassium iodide and potassium iodate in the presence of hydrochloric acid gives the compound of the present invention, 2-cyclohexyl-4-iodo-1,5-dimethyl-1,2-dihydro-3H-pyrazol-3-one, III.

The preparation of the compound of this invention, together with its herbicidal properties, is further illustrated in the following specific examples, which are provided only by way of illustration and not of limitation. Unless otherwise specified, all temperatures are in degrees centigrade, and concentration of liquid volume was carried out under the reduced pressure produced by a water aspirator.

EXAMPLE I

Synthesis of 2-Cyclohexyl-4-iodo-1,5-dimethyl-1,2-dihydro-3H-pyrazol-3-one

1. Preparation of 2-cyclohexyl-3-hydroxy-5-methylpyrazole

A solution of ethyl acetoacetate (26 g) and cyclohexylhydrazine oxalate (40 g) in ethanol (100 ml) was heated at sufficient temperature and in a manner to allow removal of the ethanol by distillation. The temperature was gradually raised to about 130°, and heating was continued at this temperature for 4 hours, during which time by-product water and additional ethanol were continuously removed by distillation. The reaction mixture, after cooling to room temperature, was dissolved in methylene chloride and extracted with a saturated solution of sodium bicarbonate. The methylene chloride layer was dried and concentrated to give a viscous residue, which was induced to crystallize upon trituration with diethyl ether. The solid was collected to give 2-cyclohexyl-3-hydroxy-5-methylpyrazole (16.5 g), m.p. 153°. The assigned structure of the product as consistent with its infrared spectrum.

2. Methylation of 2-cyclohexyl-3-hydroxy-5-methylpyrazole

A mixture of 2-cyclohexyl-3-hydroxy-5-methylpyrazole (16.5 g) and dimethyl sulfate (10.9 g) was heated with stirring at 150°–160° for 6 hours and then allowed to cool to room temperature. A solution of sodium carbonate (6.5 g) in water (100 ml) was added, and the reaction mixture was heated at reflux temperature for 2 hours, cooled, and extracted with chloroform. The layer was dried and concentrated to give a dark oil, which was dissolved in methylene chloride, treated with charcoal and diatomaceous earth, filtered and concentrated. The concentrate was fractionally distilled, and the portion distilling at 118°/0.020 mm Hg was further purified by column chromatography on silica gel. Elution with chloroform-ethyl acetate (7:3), chloroform-ethyl acetate gradients, ethyl acetate, and ethanol afforded product from the ethyl acetate-rich chloroform-ethyl acetate gradient fractions and the ethyl acetate and ethanol fractions as determined by thin-layer chromatography and nuclear magnetic resonance spectroscopy. Product-rich fractions which were shown by gas chromatography to be highly pure were combined and concentrated to give 2-cyclohexyl-1,5-dimethyl-1,2-dihydro-3H-pyrazol-3-one (3.0 g) as an oil. The assigned structure was confirmed by infrared and nuclear magnetic resonance spectral analysis.

3. Iodination of 2-cyclohexyl-1,5-dimethyl-1,2-dihydro-3H-pyrazol-3-one

A mixture of 2-cyclohexyl-1,5-dimethyl-1,2-dihydro-3H-pyrazol-3-one (2.3 g), potassium iodide (1.4 g) and potassium iodate (0.85 g) in water was heated to 100° with stirring. To the hot reaction mixture was added dropwise an aqueous solution of hydrochloric acid (0.012 moles), prepared by diluting 1.1 g of concentrated hydrochloric acid with a small amount of water. The reaction mixture was cooled, extracted with chloroform, and the chloroform extract washed successively with aqueous solutions of sodium bicarbonate and sodium thiosulfate, then dried and concentrated to give, after recrystallization from ethyl acetate-hexane, 2-cyclohexyl-4-iodo-1,5-dimethyl-1,2-dihydro-3H-pyrazol-3-one (2.1 g), m.p. 99°–100°.

Analysis: Calc'd for $C_{11}H_{17}IN_2O$: C 41.27; H 5.35; N 8.75. Found: C 41.27; H 5.19; N 8.81.

EXAMPLE II

Selective Herbicidal Activity

Preemergence Application: The preemergence herbicidal activity of 2-cyclohexyl-4-iodo-1,5-dimethyl-1,2-dihydro-3H-pyrazol-3-one, the compound of the present invention, was demonstrated as follows: Seeds of rice (*Oryza sativa*), flax (*Linum Usitatissimum*), safflower (*Carthamus tinctorius*), tomato (*Lycopersicon esculentum*), peanut (*Arachis hypogaea*), wheat (*Triticum aestivum*), morningglory (*Spomoea purpurea*), sugar beet (*Beta vulgaris*), lima bean (*Phaseolus lunatus*), corn (*Zea mays*), soybean (*Glycine max*), oat (*Avena sativa*), sorghum (*Sorghum vulgare*), barley (*Hordeum vulgare*), cotton (*Gossypium hirsutum*), sicklepod (*Cassia obtusifolia*), barnyardgrass (*Echinochloa crus-galli*), and foxtail (*Setaria faberi*) were planted in shallow flatbed trays containing about a 4 cm depth of sandy loam soil. Within twenty-four hours after planting the test compound was sprayed on the soil as an aqueous-acetone solution, at rates equivalent to 0.56, 1.12, 2.24, and 4.48 kilograms per hectare. Test plants and untreated control plants were maintained in a greenhouse and watered regularly for two to three weeks, after which time the phytotoxicity of the test compound was recorded. Individual plant species were examined for present kill and vigor. Results are presented in Table I.

In preemergence application, the compound of the present invention exhibits outstanding selectivity in favor of corn and cotton and significant selectivity in favor of peanuts.

Postemergence Application: Postemergence herbicidal activity of 2-cyclohexyl-4-iodo-1,5-dimethyl-1,2-dihydro-3H-pyrazol-3-one was determined on the same plant species using the techniques described above, except that chemical treatment was delayed until the first trifoliate leaves of the bean plants were unfolding. The treated plants were maintained in the greenhouse and watered regularly for an additional ten to fourteen days, after which time the phytotoxicity of the test compound was recorded as in the preemergence test described above. Results of this test are summarized in Table 2.

In postemergence application the compound of the present invention exhibits outstanding selectivity in favor of cotton and lesser selectivity in favor of rice and sorghum.

Table 1

Preemergence Herbicidal Activity of 2-Cyclohexyl-4-iodo-1,5-dimethyl-1,2-dihydro-3H-pyrazol-3-one

| Plant Species | Percent Kill at Indicated Rate (kg/hectare) | | | |
|---|---|---|---|---|
| | 0.56 | 1.12 | 2.24 | 4.48 |
| Rice | 0 | 20 | 20 | 60 |
| Flax | 40 | 100 | 100 | 100 |
| Safflower | 0 | 60 | 100 | 100 |
| Tomato | 0 | 60 | 100 | 100 |
| Peanut | 0 | 0 | 20 | 20 |
| Wheat | 0 | 100 | 100 | 100 |
| Morningglory | 20 | 100 | 100 | 100 |
| Sugar beet | 100 | 100 | 100 | 100 |
| Lima bean | 25 | 100 | 100 | 100 |
| Corn | 0 | 0 | 0 | 60 |
| Soybean | 0 | 30 | 100 | 100 |
| Oat | 0 | 20 | 100 | 100 |

Table 1-continued
Preemergence Herbicidal Activity of
2-Cyclohexyl-4-iodo-1,5-dimethyl-
1,2-dihydro-3H-pyrazol-3-one

| Plant Species | Percent Kill at Indicated Rate (kg/hectare) | | | |
| --- | --- | --- | --- | --- |
|  | 0.56 | 1.12 | 2.24 | 4.48 |
| Sorghum | 0 | 30 | 75* | 100 |
| Barley | 100 | 100 | 100 | 100 |
| Cotton | 0 | 0 | 0 | 100 |
| Sicklepod | 0 | 80* | 100 | 100 |
| Barnyardgrass | 0 | 20 | 100 | 100 |
| Foxtail | 20 | 100 | 100 | 100 |

*Plants remaining alive are severely damaged and are not expected to recover.

Table 2
Postemergence Herbicidal Activity of
2-Cyclohexyl-4-iodo-1,5-dimethyl-
1,2-dihydro-3H-pyrazol-3-one

| Plant Species | Percent Kill at Indicated Rate (kg/hectare) | | | |
| --- | --- | --- | --- | --- |
|  | 0.56 | 1.12 | 2.24 | 4.48 |
| Rice | 0 | 0 | 60 | 60 |
| Flax | 60 | 100 | 100 | 100 |
| Safflower | 0 | 100 | 100 | 100 |
| Tomato | 100 | 100 | 100 | 100 |
| Peanut | 0 | 30 | 100 | 100 |
| Wheat | 0 | 60 | 100 | 100 |
| Morningglory | 0 | 0 | 100 | 100 |
| Sugar beet | 100 | 100 | 100 | 100 |
| Lima bean | 50 | 100 | 100 | 100 |
| Corn | 0 | 60 | 60* | 100 |
| Soybean | 0 | 60 | 100 | 100 |
| Oat | 0 | 50 | 100 | 100 |
| Sorghum | 0 | 0 | 100 | 100 |
| Barley | 30 | 30 | 100 | 100 |
| Cotton | 0 | 0 | 0 | 100 |
| Sicklepod | 0 | 100 | 100 | 100 |
| Barnyardgrass | 60 | 100 | 100 | 100 |
| Foxtail | 0 | 0 | 80* | 100 |

*Plants remaining alive are severely damaged and are not expected to recover.

For herbicidal applications, the compound of this invention may be utilized in diverse formulations, including the agriculturally acceptable adjuvants and carriers normally employed to facilitate the dispersion of active ingredients in agricultural applications, recognizing the fact that the formulation and mode of application of a toxicant may affect the activity of the material in a given application. Thus, 2-cyclohexyl-4-iodo-1,5-dimethyl-1,2-dihydro-3H-pyrazol-3-one may be formulated as a granule of relatively large particle size, as a dust, as a wettable powder, as an emulsifiable concentrate, as a solution, or as any of several other known types of formulations, depending on the desired mode of application. For preemergence application, these herbicidal compositions are usually applied either as sprays, dusts, or granules in the area in which control of vegetation is desired. For postemergence control of established plant growth, sprays or dusts are commonly used.

Granular formulations are particularly useful for aerial distribution or for penetration of a canopy of foliage. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient, or a solution of active ingredient in a solvent, onto the surface of a generally nonabsorbent particle. The core may be water-soluble such as prilled fertilizer, or insoluble such as sand, marble chips, or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die, or by use of a granulating disc. Granular formulations may vary widely in concentration, with useful formulations containing as little as 0.5% or as much as 95% of active ingredient.

Dusts are admixtures of the active ingredient with finely divided solids such as talc, attapulgite clay, kieselguhr, and other organic and inorganic solids which act as dispersants and carriers for the toxicant; these finely divided solids have an average particle size of less than about 50 microns. A typical dust formulation, useful herein, is one containing 1.0 part of 2-cyclohexyl-4-iodo-1,5-dimethyl-1,2-dihydro-3H-pyrazol-3-one and 99.0 parts of talc.

Wettable powders, also useful formulations for both pre- and postemergence herbicides, are in the form of finely divided particles which disperse readily in water or other dispersants. The wettable powder is ultimately applied to the soil either as a dry dust or as an emulsion in water or other liquid. Typical carriers for wettable powders include fuller's earth, kaolin clays, silicas, and other highly absorbent, readily wet inorganic diluents. Wettable powders normally are prepared to contain about 5% to 80% of active ingredient, depending on the absorbency of the carrier, and usually also contain a small amount of a wetting, dispersing, or emulsifying agent to facilitate dispersion. For example, a useful wettable powder formulation contains 80.0 parts of 2-cyclohexyl-4-iodo-1,5-dimethyl-1,2-dihydro-3H-pyrazol-3-one, 17.9 parts of palmetto clay, and 1.0 part of sodium lignosulfonate and 0.3 part of sulfonated aliphatic polyester as wetting agents.

Emulsifiable concentrates, useful for herbicidal applications, are homogeneous liquid or paste compositions, dispersible in water or other dispersant. They may consist entirely of the active ingredient and a liquid or solid emulsifying agent, or they may contain a liquid carrier such as xylene, heavy aromatic naphthas, isophorone, or other nonvolatile organic solvents. For herbicidal application, these concentrates are dispersed in water or other liquid carrier, and normally applied as a spray to the area to be treated. The percentage by weight of the essential active ingredient may vary according to the manner in which the composition is to be applied, but in general comprises 0.5% to 95% of active ingredient by weight of the herbicidal composition.

Typical wetting, dispersing, or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface-active agents, many of which are available in commerce. The surface-active agent, when used, normally comprises from 1% to 15% by weight of the herbicidal composition.

These formulations may be applied without further dilution or as dilute solutions, emulsions, or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compound of this invention may be formulated and/or applied with insecticides, fungicides, nematicides, plant-growth regulators, fertilizers, and other agricultural chemicals. In applying the active compound of this invention, whether formulated alone or with other agricultural chemicals, an effective amount and concentration of 2-cyclohexyl-4-iodo-1,5-dimethyl-1,2-dihydro-3H-pyrazol-3-one is of course employed.

It is apparent that various modifications may be made in the formulation and application of the novel compound of this invention, without departing from the inventive concept herein, as defined in the following claims.

We claim:

1. 2-Cyclohexyl-4-iodo-1,5-dimethyl-1,2-dihydro-3H-pyrazol-3-one.

2. An herbicidal composition comprising an herbicidally effective amount of the compound of claim 1 in admixture with an agriculturally acceptable carrier.

3. A method of controlling undesired plant growth which comprises applying to the locus where control is desired an herbicidally effective amount of the compound of claim 1.

* * * * *

UNITED STATES PATENT AND TRADEMARK OFFICE
CERTIFICATE OF CORRECTION

PATENT NO. : 4,115,096

DATED : September 19, 1978

INVENTOR(S) : Robert Earl Sticker

It is certified that error appears in the above-identified patent and that said Letters Patent are hereby corrected as shown below:

Column 2, line 11, "ingr3edient" should read --ingredient--.
Column 3, line 35, "The layer" should read --The chloroform layer--.  Column 4, line 13, "Usitatissimum)," should read --usitatissimum),--; line 30, "present" should read --percent--.
Column 6, line 32, "80.0" should read --80.8--.

Signed and Sealed this

Ninth Day of January 1979

[SEAL]

Attest:

RUTH C. MASON
Attesting Officer

DONALD W. BANNER
Commissioner of Patents and Trademarks